United States Patent [19]
Kirshenbaum

[11] Patent Number: 6,148,265
[45] Date of Patent: Nov. 14, 2000

[54] VALENCE CORRECT MOLECULAR STRUCTURES USING CELLULAR ENCODING

[75] Inventor: Evan R. Kirshenbaum, Mountain View, Calif.

[73] Assignee: Hewlett-Packard Company, Palo Alto, Calif.

[21] Appl. No.: 09/385,127

[22] Filed: Aug. 27, 1999

[51] Int. Cl.[7] ........................... G01N 31/00; G06F 19/00; G01B 3/00
[52] U.S. Cl. ........................... 702/27; 364/578; 364/496; 395/919; 395/920
[58] Field of Search ..................... 364/578, 496, 364/497, 499, 223.4, 924.3; 395/919, 920, 119; 702/27

[56] References Cited

U.S. PATENT DOCUMENTS

| | | | |
|---|---|---|---|
| 5,386,507 | 1/1995 | Teig et al. | 395/161 |
| 5,572,439 | 11/1996 | Nishida et al. | 364/496 |
| 5,867,397 | 2/1999 | Koza et al. | 364/489 |

Primary Examiner—John S. Brusca
Assistant Examiner—Stephen Siu

[57] ABSTRACT

A method for developing a valence correct molecular structure using cellular encoding in which a set of basic types are determined for a set of basic components of the valence correct molecular structure. Each of a set of development operators for developing the valence correct molecular structure are associated with one or more of the basic types and an organism having a tree arrangement of the development operators is generated by matching the basic types associated with connections among the development operators in the tree. The matching among typed development operators reduces the likelihood of creating an unfit organism. The development of a valence correct molecular structure using cellular encoding may be used in conjunction with genetic programming to evolve a molecular structure. The type matching reduces the likelihood of creating unfit child organisms, thereby increasing the likelihood and speed of convergence to a solution for a desired valence correct molecular structure.

12 Claims, 8 Drawing Sheets

VALENCE CORRECT MOLECULAR STRUCTURES USING CELLULAR ENCODING

BACKGROUND OF THE INVENTION

1. Field of Invention

The present invention pertains to the field of designing molecular structures. More particularly, this invention relates to the design of valence correct molecular structures using cellular encoding.

2. Art Background

A variety of design problems commonly involve the development or discovery of molecular structures that yields a desire result. For example, the problem of developing or discovering a drug commonly involves a search for a molecular structure that has a desired effect or property. Other design problems may involve finding a molecular structure having a desired set of properties such as strength, conductivity, etc. Still other design problems may involve finding a molecular structure having particular taste, binding properties, etc.

Typically, such molecular structures are developed by hand using techniques in which chemists posit valence correct molecular structures as solutions for a design problem and then test the solutions using simulation or physical testing. The search space of potential molecular structures that are evaluated when solving such design problems is usually extremely large. Unfortunately, prior techniques for generating valence correct molecular structures and evaluating them as possible solutions usually require extensive time and manpower due to the large search space.

SUMMARY OF THE INVENTION

A method for developing a valence correct molecular structure using cellular encoding. The method involves determining a set of basic types for a set of basic components of a valence correct molecular structure. A set of development operators for developing the valence correct molecular structure are associated with each of one or more of the basic types. An organism having a tree arrangement of the development operators is generated by matching the basic types associated with connections among the development operators in the tree. The matching among typed development operators reduces the likelihood of creating an unfit organism.

The development of a valence correct molecular structure using cellular encoding with typed development operators may be used in conjunction with genetic programming to evolve a molecular structure having desired properties. For example, a population of organisms for developing a molecular structure may be generated and a set of parent organisms may be selected from the population based on their fitness in generating the molecular structure. A set of child organisms may then be generated by combining portions of the parent organisms such that connections among the development operators in the child organisms match the associated basic types. The type matching reduces the likelihood of creating unfit child organisms, thereby increasing the likelihood and speed of convergence to a solution for a desired valence correct molecular structure.

Other features and advantages of the present invention will be apparent from the detailed description that follows.

BRIEF DESCRIPTION OF THE DRAWINGS

The present invention is described with respect to particular exemplary embodiments thereof and reference is accordingly made to the drawings in which.

DETAILED DESCRIPTION

Figure 1:
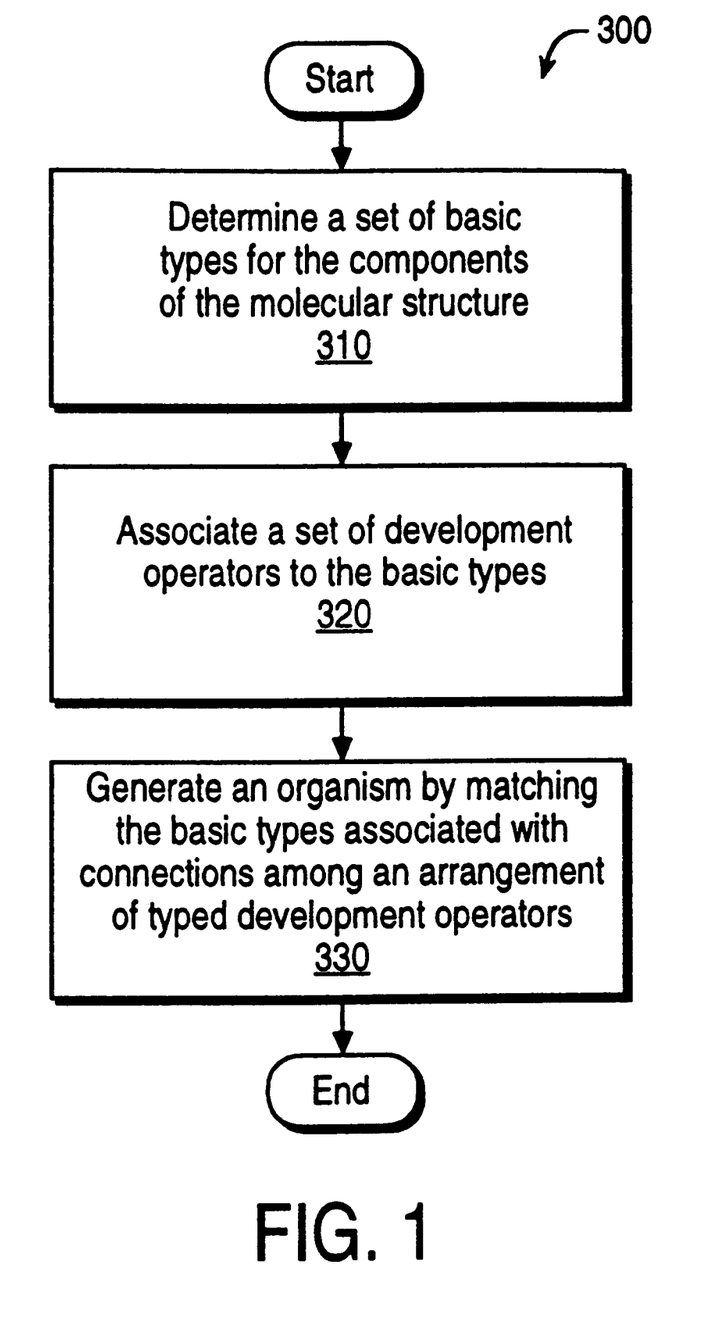
FIG. 1 illustrates a method for developing a valence correct molecular structure using cellular encoding.

FIG. 1 illustrates a method 300 for developing a valence correct molecular structure using cellular encoding. A molecular structure developed using the method 300 may be viewed as an arrangement of atoms and bonds with each atom having an associated valence and each bond having an associated weight.

At step 310, a set of basic types for the components of a molecular structure are determined. In one embodiment, the basic types determined at step 310 include a basic atom type and a basic bond type. The basic atom type includes a set of subtypes which are referred to as $atom_i$ representing an atom of valence equal to i (where i=0, 1, 2 . . . ). The basic bond type includes a set of subtypes which are referred to as $bond_j$ representing a bond of weight equal to j (where j=1, 2, 3 . . . ). The maximum valence considered in evolving the molecular structure is referred to as V.

At step 320, each of a set of development operators for developing a valence correct molecular structure is associated with one or more of the basic types determined at step 310. As a consequence of this association between development operators and basic types, the development operators may be referred to as typed development operators. A development operator that is associated with a particular basic type is said to be typed for the particular basic type. A typed development operator may specify one or more child development operators for further developing the structure.

In one embodiment, the typed development operators for developing a valence correct molecular structure are arranged in a set of classes. These classes include a class of atom identification operators, a class of atom addition operators, a class of atom interpolation operators, a class of bond split operators, a class of ring interpolation operators, and a class of end operators. The atom identification operators and the atom addition operators act on atom types and atom sub types and are associated with the basic types $atom_i$ at step 320. The atom interpolation operators, the bond split operators, the ring interpolation operators, and the end operators act on bond types and bond sub types and are associated with the basic types $bond_j$ at step 320.

The class of atom identification operators generate a set of labels for each valence level that provide the correct name for atoms of the appropriate valence. In one embodiment, for example, the atom identification operators include the following. The atom identification operators that apply to the basic type $atom_4$ generate a label from a set that includes H, F, Na, and Cl. The atom identification operators that apply to the basic type $atom_2$ generate a label from a set that includes O and S. The atom identification operators that apply to the basic type $atom_3$ generate a label from a set that includes N and P. The atom identification operators that apply to the basic type $atom_4$ generate a label from a set that includes C and Si. The atom identification operators that apply to the basic type $atom_5$ generate a label from a set that includes Al. The atom identification operators that apply to the basic type $atom_0$ generate a label from a set that includes He and Ne. The choice among this overall set of operators is a step that parameterizes an experiment with the types of atoms that will be considered.

In one embodiment, the atom identification operators terminate the development of atom components and therefore have no child development operators. In other embodiments, development continues until a special end operator is encountered.

The atom identification operators H, F, Na, and Cl are associated with the basic type $atom_1$ at step 320. Similarly, the atom identification operators O and S are associated with the basic type $atom_2$, and the atom identification operators N and P are associated with the basic type $atom_3$, etc., at step 320.

Figure 2A:
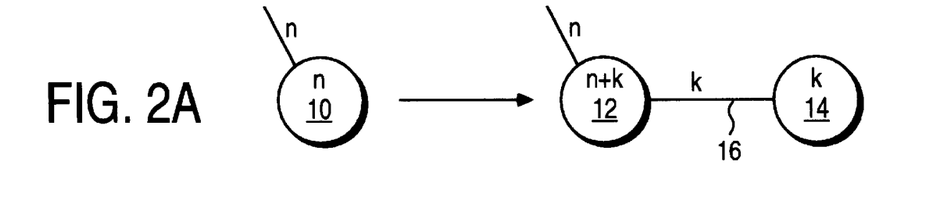
FIGS. 2a–2d illustrate one embodiment of the typed development operators used to develop a valence correct molecular structure from an embryonic structure.

FIG. 2a illustrates the class of atom addition operators. The atom addition operators (ATOM_ADD(n,k)) apply to an atom 10 of valence equal to n and add an atom of valence equal to k to it, thereby resulting in an atom 12 of valence equal to n+k (replacing the original atom 10 and retaining all if its bonds), a bond 16 of weight equal to k and an atom 14 of valence equal to k. There is one such atom addition operator for each $n \geq 0$, $k \geq 1$ such that $n+k \leq V$. For example, the ATOM_ADD(1,1) operator applies to an atom of basic type $atom_1$ and adds an of basic type $atom_1$ to it, the ATOM_ADD(1,2) operator applies to an atom of basic type $atom_1$ and adds an atom of basic type $atom_2$ to it, and the ATOM_ADD(2,1) operator applies to an atom of basic type $atom_2$ and adds an atom of basic type $atom_1$ to it.

The ATOM_ADD(1,1) and the ATOM_ADD(1,2), etc., operators are associated with the basic type $atom_1$ at step 320. Similarly, the ATOM_ADD(2,1) and the ATOM_ADD(2,2), etc., operators are associated with the basic type $atom_2$ at step 320 and the ATOM_ADD(4,1) and the ATOM_ADD(4,2), etc., operators are associated with the basic type $atom_4$ at step 320.

Each ATOM_ADD(n,k) operator has three typed child operators for further developing the structures that it yields. The three child operators include a first child operator which is associated with the basic type $atom_{n+k}$ for further developing the atom 12, a second child operator which is associated with the basic type $bond_k$ for further developing the bond 16, and a third child operator which is associated with the basic type $atom_k$ for further developing the atom 14.

Figure 2B:
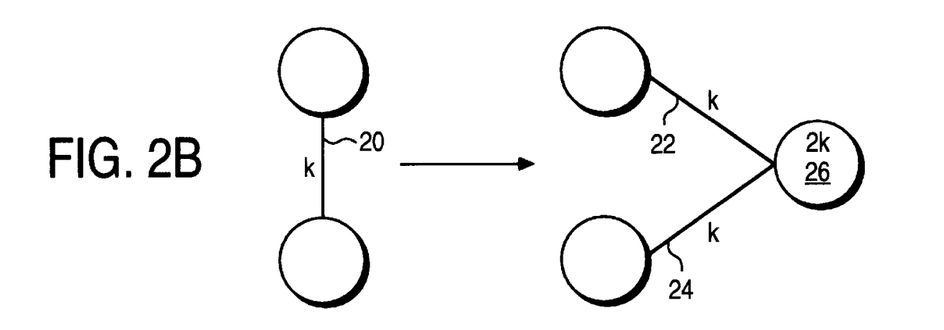

FIG. 2b illustrates the class of atom interpolation operators. The atom interpolation operators (ATOM_INTERP (k)) apply to a bond 20 of weight equal to k and interpolate an atom of valence equal to 2k, thereby resulting in a pair bonds 22–24 each having a weight equal to k and an atom 26 of valence equal to 2k. There is one such atom interpolation operator for each $1 \leq k \leq V/2$. For example, the ATOM_INTERP(1) operator applies to a bond of basic type $bond_1$, and the ATOM_INTERP(2) operator applies to a bond of basic type $bond_2$.

The ATOM_INTERP(1) operator is associated with the basic type $bond_1$ at step 320. Similarly, the ATOM_INTERP(2) operator is associated with the basic type $bond_2$, and the ATOM_INTERP(3) operator is associated with the basic type $bond_3$, etc., at step 320.

Each ATOM_INTERP(k) operator has three typed child operators for further developing the structures that it yields. The three child operators include a first child operator which is associated with the basic type $bond_k$ for further developing the bond 22, a second child operator which is associated with the basic type $atom_{2k}$ for further developing the atom 26, and a third child operator which is associated with the basic type $bond_k$ for further developing the bond 24.

Figure 2C:
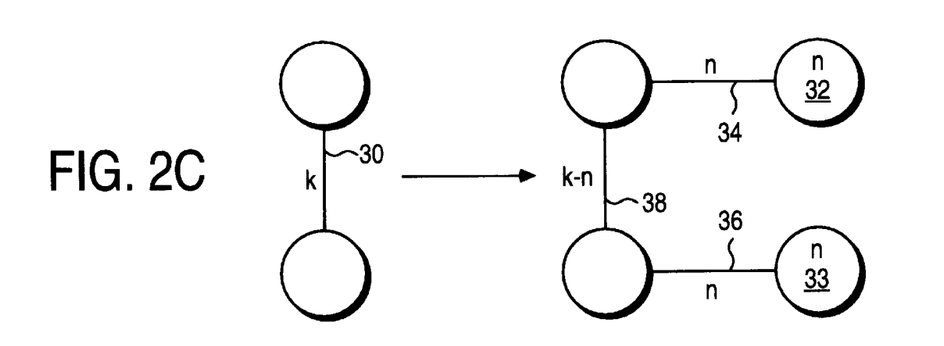

FIG. 2c illustrates the class of bond split operators. The bond split operators (BOND_SPLIT(k,n)) apply to a bond 30 of weight equal to k and sheds weight equal to n, creating a new atom of valence equal to n attached to the atoms on each end of the current bond. This results in a pair of atoms 32–33 of valence equal to n, a pair of bonds 34–36 of weight equal to n, and a bond 38 of weight equal to k−n. There is one such bond split operator for each $n \geq 1$, $k > n$. For example, the BOND_SPLIT(2,1) operator applies to a $bond_2$ and sheds weight equal to 1, the BOND_SPLIT(3,2) operator applies to a $bond_3$ and sheds weight equal to 2, and the BOND_SPLIT(3,1) operator applies to a $bond_3$ and sheds weight equal to 1.

The BOND_SPLIT(2,1) operator is associated with the basic type $bond_2$ at step 320 and the BOND_SPLIT(4,1) and the BOND_SPLIT(4,2), etc., operators are associated with the basic type $bond_4$ at step 320.

Each BOND_SPLIT(k,n) operator has five typed child operators for further developing the structures that it yields. The five child operators include a first child operator which is associated with the basic type $atom_n$ for further developing the atom 32, a second child operator which is associated with the basic type $atom_n$ for further developing the atom 33, and a third child operator which is associated with the basic type $bond_n$ for further developing the bond 34, a fourth child operator which is associated with the basic type $bond_n$ for further developing the bond 36, and fifth child operator which is associated with the basic type $bond_{k-n}$ further developing the bond 38.

Figure 2D:
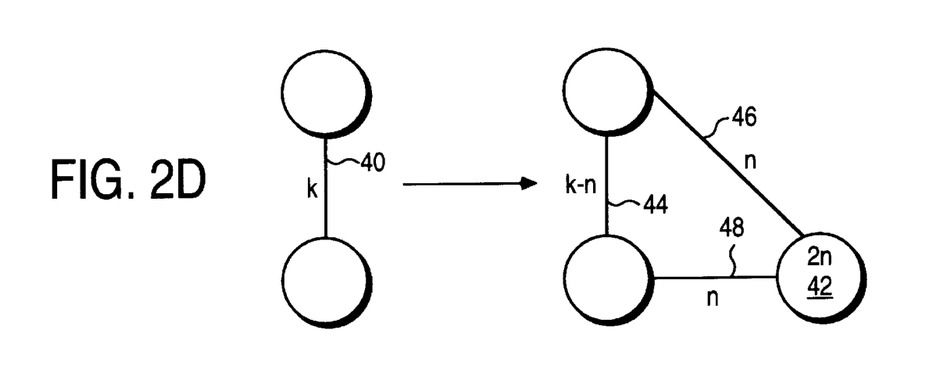

FIG. 2d illustrates the class of ring interpolation operators. The ring interpolation operators (RING_INTERP(k, n)) apply to a bond 40 of weight equal to k and convert it to a bond of weight equal to k−d interpolate an atom of valence equal to 2n along a path parallel to the bond 40. This results in an atom 42 of valence equal to 2n, a bond 44 of weight equal to k−n, and a pair of bonds 46–48 each of weight equal to n. There is one such ring interpolation operator for each $1 \leq n < k$, $2n \leq V$. For example, the RING_INTERP(3,1) operator applies to a $bond_3$ and interpolates an $atom_2$, and the RING_INTERP(2,1) operator applies to a $bond_2$ and interpolates an $atom_2$.

The RING_INTERP(2,1) operator is associated with the basic type $bond_2$ at step 320 and the RING_INTERP(4,1) and the RING_INTERP(4,2), etc., operators are associated with the basic type $bond_4$ at step 320.

Each RING_INTERP(k,n) operator has four typed child operators for further developing the structures that it yields. The four child operators include a first child operator which is associated with the basic type $bond_n$ for further developing the bond 46, a second child operator which is associated with the basic type $atom_{2n}$ for further developing the atom 42, and a third child operator which is associated with the basic type $bond_n$ for further developing the bond 48, and a fourth child operator which is associated with the basic type $bond_{k-n}$ for further developing the bond 44.

The class of end operators (END) apply to a bond of any weight. The end operators cease further development and therefore have no child operators. The END operator is associated with the basic types bond$_i$ for all valid values for i at step 320.

At step 330, an organism having a tree arrangement of typed development operators is generated by matching the basic types associated with connections among the development operators in the tree. For example, a development operator that specifies a child operator that is typed for the development of the basic type atom$_1$ is type matched if connected to a development operator that is typed for the atom$_1$ basic type but not if connected to a development operator that is typed for the atom$_2$ basic type or the bond$_1$ basic type.

The arrangement of typed development operators in an organism defines a program for developing a valence correct molecular structure from an embryo structure. In one embodiment, the embryo structure is an unidentified noble gas, i.e. an atom with valence equal to 0 (atom$_0$). An organism is generated at step 330 so that each typed development operator in the organism operates on a component of the appropriate basic type. For example, development operators that are typed for atom$_1$ components operate only on atom$_1$ components and development operators that are typed for atom$_2$ components operate only on atom$_2$ components. Each development operator modifies or adds new components or replicates components. Each modified or new or replicated component is then further developed under control of the child operators of the development operator that created them.

Figure 3:
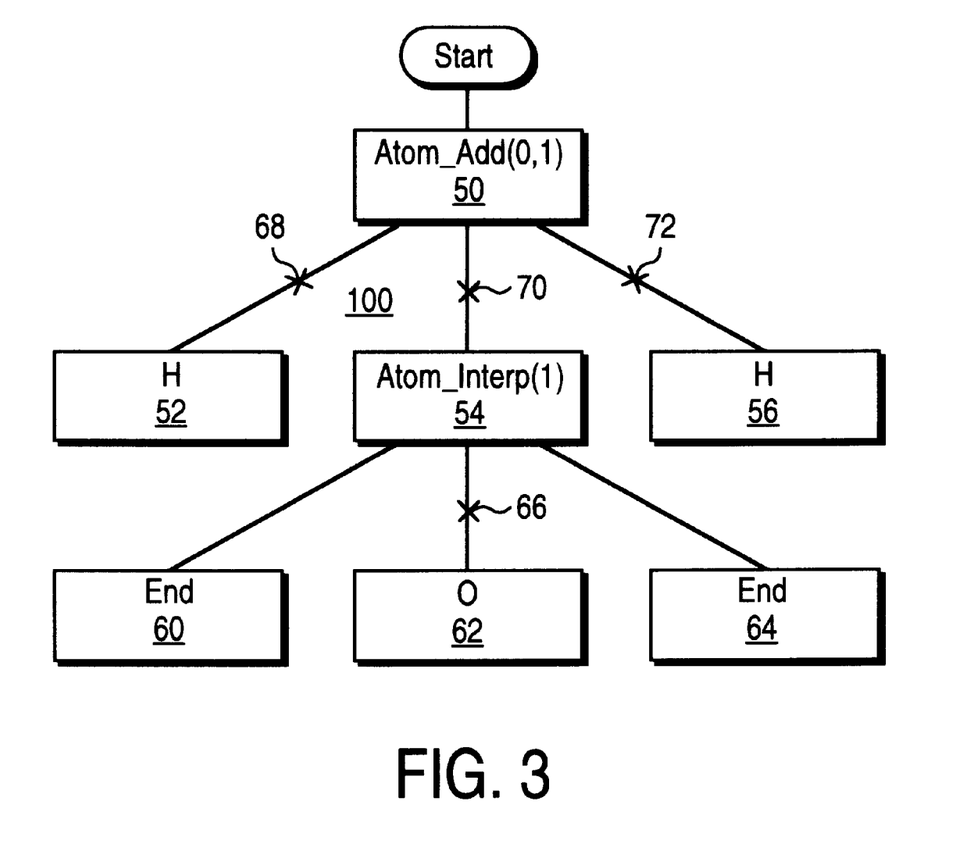
FIG. 3 shows a tree which defines a program for generating a valance correct molecular structure using cellular encoding.

FIG. 3 shows a tree 100 which defines a program for generating a valence correct molecular structure using cellular encoding. The tree 100 includes an arrangement of operator blocks 50–64 each of which holds a typed development operator. The tree 100 is generated so that the parent-child interconnections among the operator blocks 50–64 match the basic types associated with the development operators contained in the operator blocks 50–64.

The operator block 50 holds the ATOM_ADD(0,1) operator and has three children which are the H operator of type atom$_1$ in the operator block 52, the ATOM_INTERP(1) operator of type bond$_1$ in the operator block 54, and the H operator of type atom$_1$ in the operator block 56. Other legal operators for the operator block 52 include the ATOM_ADD(1,1) and the ATOM_ADD(1,2) operators each of which is of type atom$_1$. Other legal operators for the operator block 56 include the ATOM_ADD(1,1) and the ATOM_ADD(1,2) operators each of which is of type atom$_1$.

Examples of illegal operators for the operator blocks 52 and 56 include the ATOM_INTERP(1), O, and C operators. Examples of illegal operators for the operator block 54 include the ATOM_INTERP(2), ATOM_INTERP(3), and ATOM_ADD(1,1) operators.

The ATOM_INTERP(1) operator in the operator block 54 has three children which are the END operator in the operator block 60, the O operator of type atom$_2$ in the operator block 62, and the END operator in the operator block 64. Another legal operator for the operator blocks 60 and 64 include the ATOM_INTERP(1) operator. Other legal operators for the operator block 62 include the ATOM_ADD(2,1) and the ATOM_ADD(2,2) operators.

Figure 4:
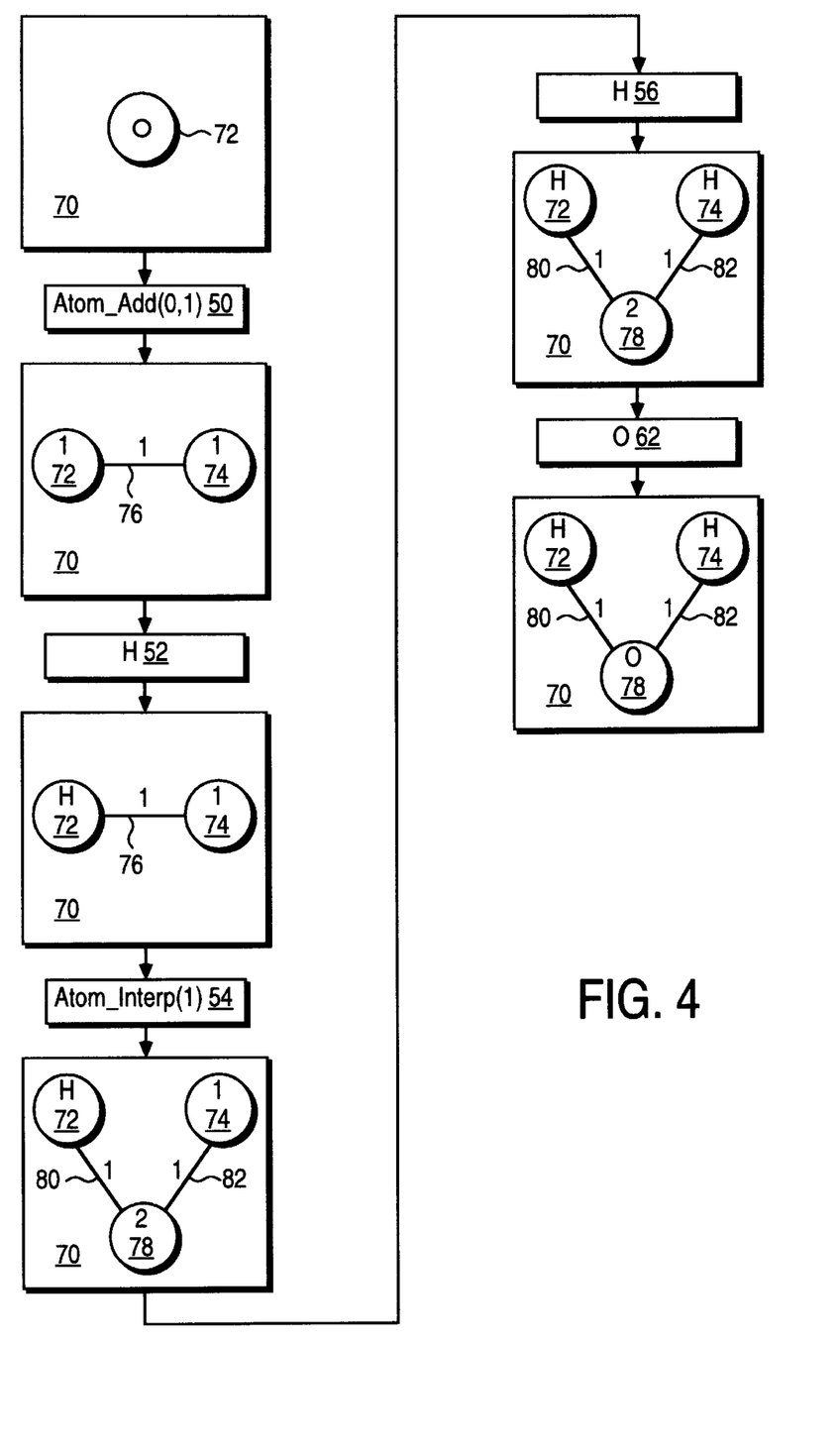
FIG. 4 illustrates the development of a valence correct molecular structure from an embryo structure by the application of the typed development operators in a tree.

FIG. 4 illustrates the development of a valence correct molecular structure 70 from an embryo structure 72 by the application of the typed development operators 50–64 in the tree 100. At the start of the tree 100, the molecular structure 70 consists of the atom 72 with valence equal to 0 as an embryonic structure.

The ATOM_ADD(0,1) operator in block 50 creates an atom 72 of valence equal to 1 and an atom 74 of valence equal to 1 with a bond 76 of weight equal to 1 from the atom 72. The first child of the ATOM_ADD(0,1) operator in block 50 is applied to the atom 72, the second child of the ATOM_ADD(0,1) operator in block 50 is applied to the bond 76, and the third child of the ATOM_ADD(0,1) operator in block 50 is applied the atom 74.

The H operator in block 52 is the first child of the ATOM_ADD(0,1) operator in block 50. The H operator in block 52 applies the label "H" to the atom 72. The ATOM_INTERP(1) operator in block 54 is the second child of the ATOM_ADD(0,1) operator in block 50. The ATOM_INTERP(1) operator in block 54 creates a pair of bonds 80–82 each of weight equal to 1 and an atom 78 of valence equal to 2. The H operator in block 56 is the third child of the ATOM_ADD(0,1) operator in block 50. The H operator in block 56 applies the label "H" to the atom 74.

The first child of the ATOM_INTERP(1) operator in block 54, the END operator in block 60, ceases further development of the bond 80. The second child of the ATOM_INTERP(1) operator in block 54, the O operator in block 62, applies the label "O" to the atom 78. The END operator in block 64, the third child of the ATOM_INTERP (1) operator in block 54, ceases further development of the bond 82.

Figure 5:
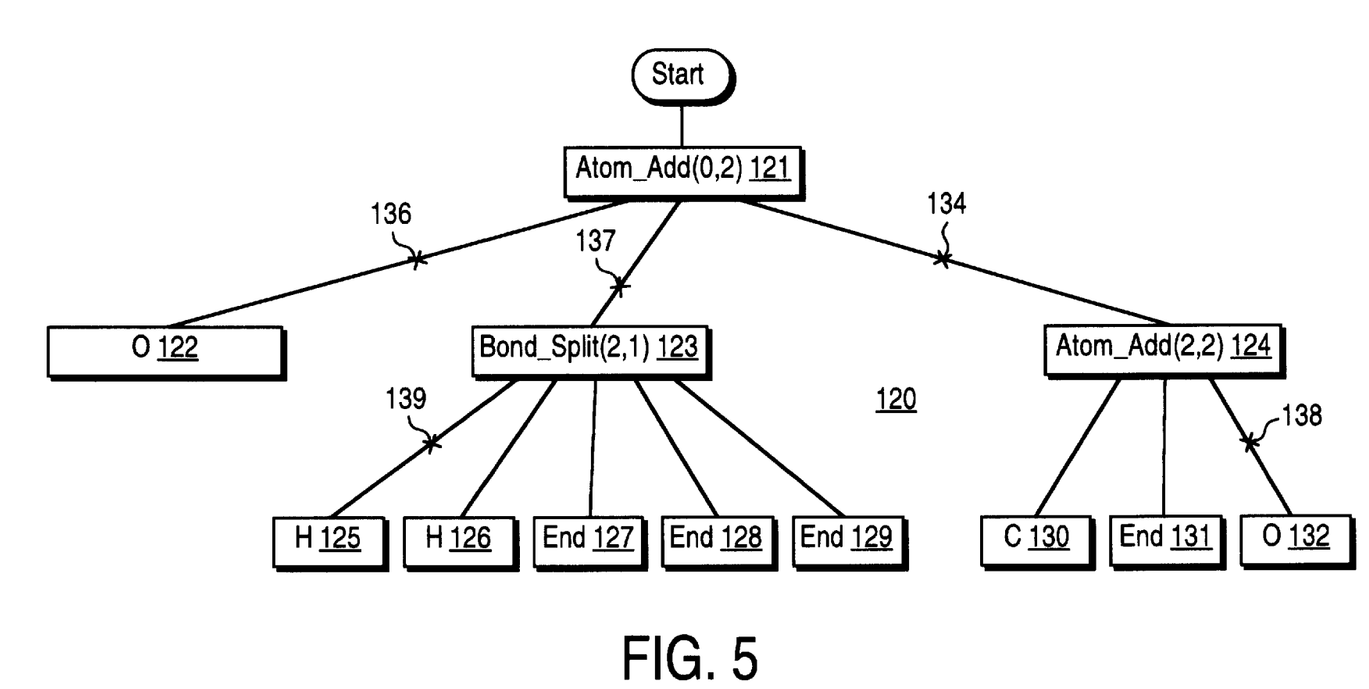
FIG. 5 shows a tree which defines another program for generating a valance correct molecular structure using cellular encoding.

FIG. 5 shows a tree 120 which defines another program for generating a valance correct molecular structure using cellular encoding. The tree 120 includes an arrangement of operator blocks 121–132 each of which holds a typed development operator. The tree 120 is generated so that the parent-child interconnections among the operator blocks 121–132 match the basic types associated with the development operators contained in the operator blocks 121–132.

Figure 6:
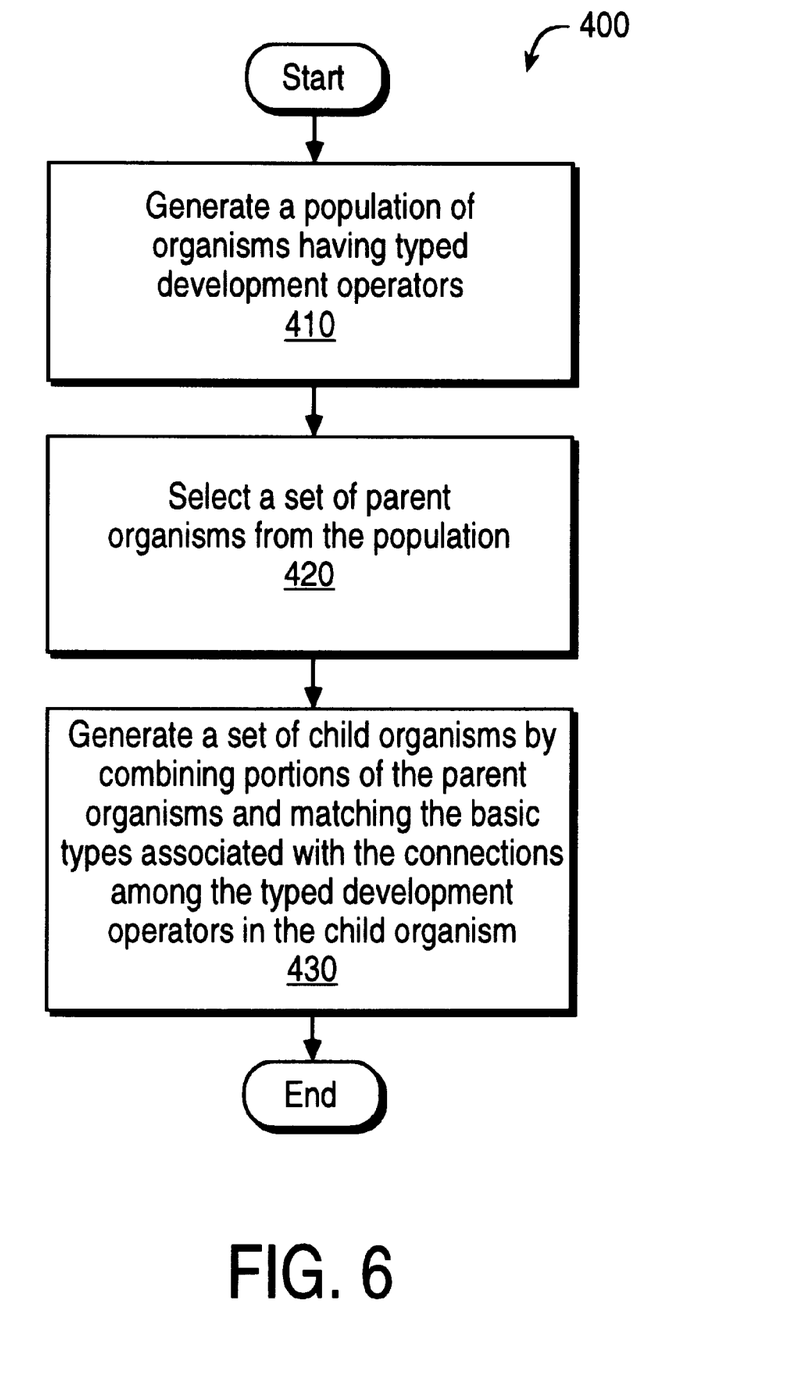
FIG. 6 illustrates a method for evolving a valance correct molecular structure using cellular encoding.

FIG. 6 illustrates a method 400 for evolving a valance correct molecular structure using cellular encoding with typed development operators. At step 410, a population of organisms having typed development operators is generated in accordance with the method 300.

At step 420, a set of parent organisms is selected from the population generated at step 410. The parent organism are selected based on the fitness of the parent organisms in generating a desired molecule. The fitness may be based a fitness measure which is determined using known techniques including automated or software simulation techniques or evaluation by physical testing of the molecules yielded by the organisms.

At step 430, a set of child organisms is generated by combining portions of the parent organisms such that the connections among the development operators in each child organism tree have matching types. The child organisms may provide a population for a subsequent iteration of the method 400.

Steps 420–430 are repeated through as many iterations as are necessary to generate an organism that yields a molecule having the desired fitness for solving a particular problem. The combining performed at step 430 my include mutation of individual trees or the cutting and combining of portions of different trees which may be referred to as crossover.

For example, the tree 100 along with the tree 120 may each be a putative solution for the problem of developing a desired molecule. The trees 100 and 120 may be organisms in an initial population or may be organisms that are generated during any iteration of the method 400. In either case, the trees 100 and 120 are selected as parents at step 420.

Figure 7:
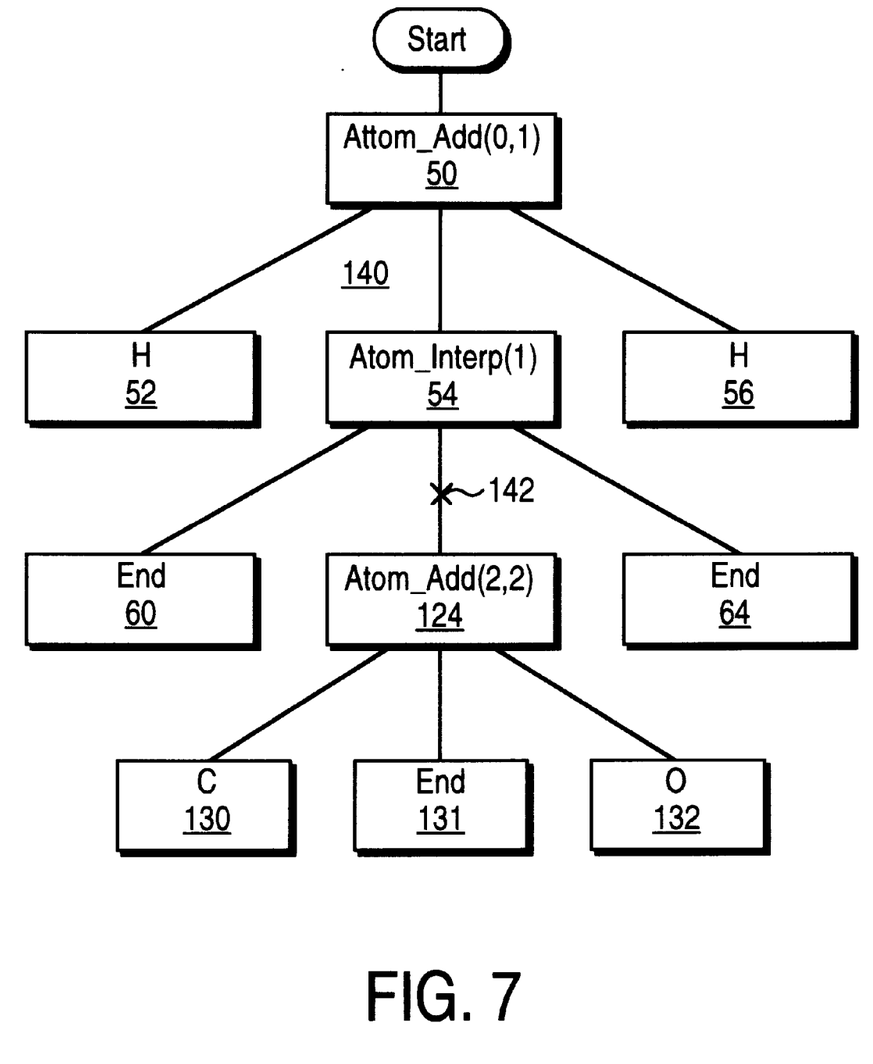
FIG. 7 shows a child tree which is generated by combining a pair of parent trees.

FIG. 7 shows a child tree 140 which is generated at step 430 by combining the trees 100 and 120. The child tree 140 is formed by cutting the tree 100 at point 66 and cutting the tree 120 at point 134. The operator blocks 50–60 and 64 from the tree 100 provide the upper portion of the child tree 140. The tree branch consisting of the operator blocks 124, and 130–132 from the tree 120 are spliced onto the child tree 140 at point 142.

The splice at point 142 is selected to match the $atom_2$ basic type required by the ATOM_INTERP(1) operator in block 54. Other tree branches that may be spliced onto points 142 of the child tree 140 include tree branches cut at points 136 and 138 from the tree 120. Both of these cuts provide the $atom_2$ basic type needed at point 142. Examples of tree branches that cannot be spliced onto point 142 of the child tree 140 under the rules of the present typed cellular encoding methods include tree branches cut at points 68, 70, and 72 from the tree 100 and tree branches cut at points 137 and 139 from the tree 120. None of these cuts provide the $atom_2$ basic type required for the second child of the ATOM_INTERP(1) operator in block 54 of the child tree 140.

Figure 8:
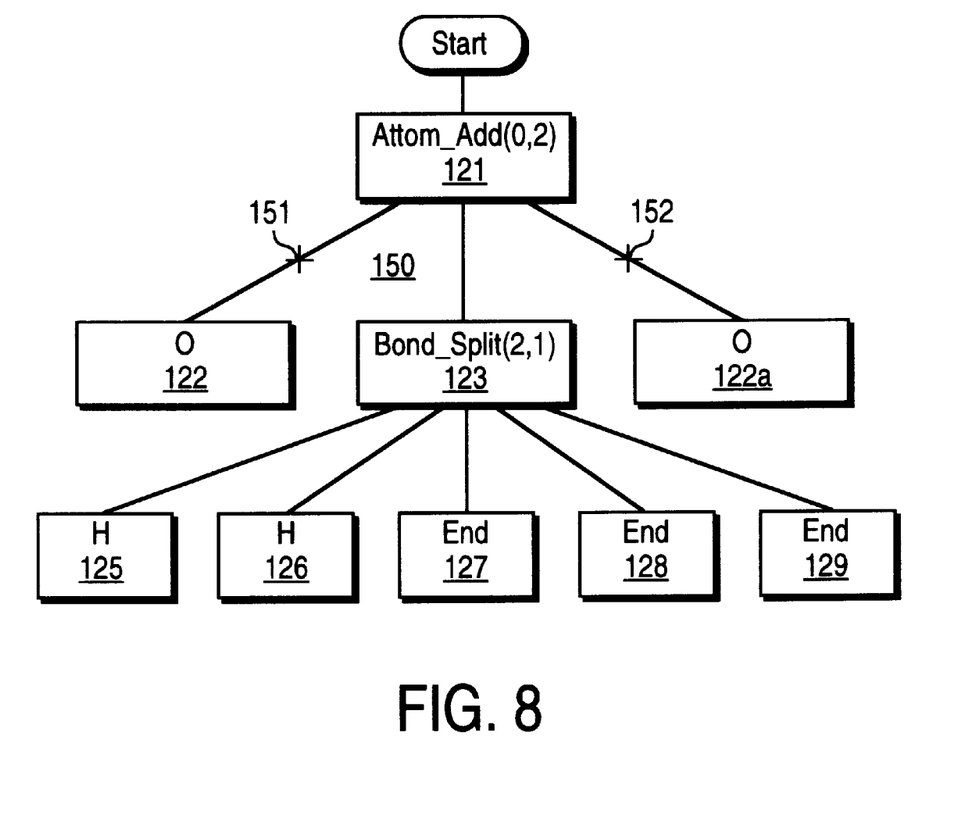
FIG. 8 shows a child tree which is generated by replicating a portion of a parent tree.

FIG. 8 shows a child tree 150 which is generated at step 430 by replicating a portion of the tree 120. The child tree 150 is formed by cutting the branch consisting of the operator blocks 124 and 130–132 from the tree 120 at point 134 and then replicating the operator block 122 as operator block 122a and splicing it to point 152 in the child tree 150. This provides the matching basic type of $atom_2$ required for the third child of the ATOM_ADD(0,2) operator in block 121. Another example is to replicate the branch consisting of the operator blocks 124 and 130–132 and splicing it onto the child tree 150 at point 150 in place of the operator block 122. This would also provide the matching basic type of $atom_2$ needed at point 150.

Although the above examples show single cuts made to a parent tree, these cellular encoding with matching typed development operator techniques may readily be adapted to methods which make multiple cuts to a parent tree when creating child organism.

Some embodiments may not employ non-empty sets of the atom identification operators for every n<V. For example, there may not be atom identification operators that apply to $atom_0$ and $atom_3$ types. Embodiments having operators that delete valence from an atom may not have atom identification operators apply to $atom_v$. An example of an operator that deletes valence is one which replaces an $atom_n$ by and $atom_{n-k}$ and an $atom_k$ by creating a new atom and shifting k-weight bonds to it.

Some embodiments may employ a ATOM_ADD(n) operator as an alternative to the ATOM_ADD(n,k) operator. The ATOM_ADD(n) operator takes a numeric expression, a child sub tree that evaluates to a numeric expression, to provide the value of k. The value is restricted to at least zero and no more then V−n. The restriction may be accomplished, for example, by replacing values by the maximum or minimum or by computing modulo V−n−1 and adding one.

Some embodiments may employ a BOND_SPLIT(n) operator as an alternative to the BOND_SPLIT(k,n) operator. The BOND_SPLIT(n) operator uses a value for n calculated by a numeric parameter limited to $1 \geq n < k$.

Some embodiments may employ a RING_INTERP(k) operator as an alternative to the RING_INTERP(k,n) operator. The RING_INTERP(k) operator uses a value for n calculated by a numeric parameter limited to $1 \geq n \geq min(k-1, V/2)$.

The foregoing detailed description of the present invention is provided for the purposes of illustration and is not intended to be exhaustive or to limit the invention to the precise embodiment disclosed. Accordingly, the scope of the present invention is defined by the appended claims.

What is claimed is:

1. A method for developing a valence correct molecular structure, comprising the steps of:

determining a set of basic types for a set of basic components of the valence correct molecular structure;

associating each of a set of development operators for cellular encoding of the valence correct molecular structure with one or more of the basic types;

generating an organism having a tree arrangement of the development operators such that each child development operator in the tree matches one of the basic types developed by the corresponding parent development operator in the tree.

2. The method of claim 1, wherein the basic components include a basic atom type and the basic types include a class of basic types for the basic atom type that includes a basic type for each of a set of possible atom valences in the valence correct molecular structure.

3. The method of claim 1, wherein the basic components include a basic bond type and the basic types include a class of basic types for the basic bond type that includes a basic type for each of a set of possible bond weights in the valence correct molecular structure.

4. The method of claim 1, wherein the development operators includes a class of atom identification operators each of which applies a label to an atom of an appropriate basic type.

5. The method of claim 1, wherein the development operators includes a class of atom addition operators each of which adds an atom to another atom of an appropriate basic type.

6. The method of claim 1, wherein the development operators includes a class of atom interpolation operators each of which interpolates an atom from a bond of an appropriate basic type.

7. The method of claim 1, wherein the development operators includes a class of bond split operators each of which creates pair of atoms from a bond of an appropriate basic type.

8. The method of claim 1, wherein the development operators includes a class of ring interpolation operators each of which interpolates an atom from a bond of an appropriate basic type.

9. The method of claim 1, wherein the development operators includes a class of end operators each of which ceases development from a bond of an appropriate basic type.

10. The method of claim 1, further comprising the steps of:

generating a population of organisms each having a tree arrangement of the development operators by matching the basic types associated with connections among the development operators in each tree;

selecting a set of parent organisms from the population of organisms;

generating a set of child organisms by combining portions of the parent organisms such that the basic types associated with connections among the development operators in the child organisms match.

11. The method of claim 10, wherein the step of selecting a set of parent organisms comprises the step of selecting a set of parent organisms based on a fitness of a set of molecular structures generated by the organisms.

12. The method of claim 10, wherein the step of generating a set of child organisms by combining portions of the parent organisms includes the steps of:

cutting a tree branch from a first one of the parent organisms;

cutting a second one of the parent organisms at a particular point;

splicing the tree branch from the first one of the parent organisms onto the second one of the parent organisms at the particular point if the basic type associated with a development operator in the tree branch at the particular point matches the basic type associated with a development operator in the second parent organism at the particular point.

* * * * *